(12) United States Patent
Paul

(10) Patent No.: US 10,222,595 B2
(45) Date of Patent: Mar. 5, 2019

(54) COMPACT FOLDED OPTICAL MULTIPASS SYSTEM

(71) Applicant: Joshua B Paul, Palo Alto, CA (US)

(72) Inventor: Joshua B Paul, Palo Alto, CA (US)

(*) Notice: Subject to any disclaimer, the term of this patent is extended or adjusted under 35 U.S.C. 154(b) by 0 days.

(21) Appl. No.: 14/757,072

(22) Filed: Nov. 12, 2015

(65) Prior Publication Data

US 2017/0139191 A1    May 18, 2017

(51) Int. Cl.
*G01N 21/00* (2006.01)
*G02B 17/00* (2006.01)
*G01N 21/03* (2006.01)

(52) U.S. Cl.
CPC ......... *G02B 17/004* (2013.01); *G01N 21/031* (2013.01)

(58) Field of Classification Search
CPC .............. G01N 21/255; G01N 21/031; G02B 19/0023; G02B 17/004; H01S 3/063; H01S 3/08081
USPC ........ 356/437, 436, 213, 432, 435; 73/24.02
See application file for complete search history.

(56) References Cited

U.S. PATENT DOCUMENTS

| | | | | |
|---|---|---|---|---|
| 3,860,818 A | * | 1/1975 | Stalder ................. | G01N 21/85 250/343 |
| 5,440,143 A | * | 8/1995 | Carangelo ............ | G01N 21/031 250/573 |
| 5,546,222 A | * | 8/1996 | Plaessmann .......... | H01S 3/2325 359/346 |
| 8,605,355 B2 | * | 12/2013 | Lundquist ......... | H01S 3/094084 359/333 |
| 2006/0193362 A1 | * | 8/2006 | Kopf ...................... | H01S 3/063 372/93 |
| 2009/0232171 A1 | * | 9/2009 | Abe ...................... | H01S 3/2232 372/25 |
| 2010/0328761 A1 | * | 12/2010 | Reid ........................ | G02F 1/39 359/330 |
| 2012/0092782 A1 | * | 4/2012 | So ........................ | G02B 17/004 359/858 |
| 2012/0287418 A1 | * | 11/2012 | Scherer .................. | G01N 21/61 356/51 |

* cited by examiner

*Primary Examiner* — Isiaka Akanbi
(74) *Attorney, Agent, or Firm* — Patent Law Offices; Daryl C. Josephson, Esq.

(57) ABSTRACT

An optical multipass system is configured to include, in addition an end-mirror configuration of reflective surfaces, a multipass pattern folding assembly. The end-mirror configuration includes at least two reflective surfaces arranged to provide for establishing cell stability of an optical multipass cell comprising all or part of the optical multipass system, or further provide for directing and/or focusing light within the optical multipass cell. The multipass pattern folding assembly includes at least two inner reflective surfaces configured to provide for folding an optical pattern intra-cavity at least twice off one of the inner reflective surfaces of the multipass pattern folding assembly.

20 Claims, 4 Drawing Sheets

COMPACT FOLDED OPTICAL MULTIPASS SYSTEM

FIELD OF THE INVENTION

The present invention relates, in general, to optical multipass systems and methods, and in particular embodiments, to providing optical multipass systems utilizing an optical pattern folding technique employing reflective surfaces to provide for one or more optical folding regions of an "intercepted" optical multipass pattern.

BACKGROUND

Optical multipass cells are often considered in terms of a typical application employing such cells, such as for in use in optical absorption or emission spectrometers. Absorption spectroscopy, for example, is widely used in many applications, including environmental monitoring, greenhouse gas and pollution monitoring, and industrial process control applications in the energy and manufacturing sectors. In gas-phase absorption spectroscopy, for example, a gas absorption spectrometer detects the presence of a targeted-gas within a subject gas-sample by passing a light beam at a selected wavelength(s) through the gas sample, and measuring the absorption (attenuation) of the light beam as a function of the light wavelength, thus enabling the quantitative determination of the concentration of the targeted-gas or gases. As the level of attenuation of the light is directly proportional to the optical path length through the gas, absorption spectroscopy sensitivity, for example, can be enhanced by increasing the effective path length via the use of an optical multipass cell. An equation describing this absorption rate as a function of path-length (L), know as Beer's Law, is given by $$I(L)/I_o = e^{-\sigma cL},$$

where $I_o$ is the initial intensity of the light, a is the absorption cross-section at the selected frequency for the absorbing species, and c is the concentration of the absorbing species.

Absorption spectroscopy is, however, merely one example of various applications of a further included optical multipass system referred to as an optical multipass cell. A typical optical multipass cell (also referred to herein as a "multipass cell") broadly includes a particular arrangement of statically and/or adjustably mounted optics that provide for receiving and directing a provided light beam (also referred to herein as a "light source") through a multipass cell inlet and cell cavity, and then outputting the result back through the inlet (the inlet also serving as an outlet) or through a separate outlet, and/or toward a window and/or so-called optical detector. In one common arrangement, the multipass cell comprises an elongated cylinder in which "end" mirrors are disposed at opposite ends of the cylinder; in some examples, only one of the end-mirrors defines a hole and the hole serves as both an inlet and outlet for the light beam, while in other examples, one end-mirror defines an inlet hole (or "inlet") for the light beam and the other end-mirror defines an outlet hole (or "outlet") for the light beam. In either case, a source light beam entering through the cell inlet is reflected along an optical path that directly connects the first end-mirror and the other end-mirror in a repetitive fashion before exiting through the outlet hole. The source light beam thus bounces repeatedly from one end-mirror directly to the other end-mirror until exiting through the outlet. The bouncing of the light beam directly between the end-mirrors acts to increase the optical length and exposure of the light to the gas or gases within the multipass cell without instead increasing the length of the cell. Multipass cells also typically employ at least one end-mirror that is concave in order to continually re-focus the light beam as it traverses the cell, thereby allowing for a stable optical pattern to be produced, and avoiding overlap and fringing/interference effects that might otherwise occur as the beam expands due to intrinsic divergence or "spreading" of the light beam.

Two underlying optical multipass cell types have long remained prevalent: the Herriott cell and the White cell. A Herriott cell type provides two opposing end-mirrors that are arranged at opposite ends of the multipass cell cavity and directed at one another. Thus, a source light beam is caused to repeatedly bounce across the length of the cell cavity—directly from one end-mirror to the other end-mirror—and thereby increasing the effective path length each time the light beam undergoes another reflection at each end mirror.

A White cell differs from a Herriott cell in that the White cell instead typically utilizes a three mirror arrangement; here two smaller concave mirrors are arranged at a first end of the multipass cell cavity so as to oppose a larger concave mirror at the second end of the multipass cell cavity. In this case, a source light beam bounces (across the length of the cell cavity) directly between the first smaller end-mirror and the larger opposing mirror and then (across the length of the cell cavity) directly between the second smaller end-mirror and the larger opposing mirror, in a repeated so-called "V" pattern, before exiting. White cells are generally considered more complex than Herriott cells but find advantages with incoherent sources such as thermal emitters.

Examples of the aforementioned optical multipass cells and multipass systems that incorporate such cells include U.S. patent application Ser. No. 11/671,364 to inventor Walter M. Doyle, which provides a mirror alignment adjustment and a mirrored viewing window based on a White cell. U.S. Pat. No. 5,440,143 to inventors Carangelo, et al. further provides a gas cell, also based on a White cell, in which at least one of the end-mirrors is formed with an added cylindrical component. U.S. patent application Ser. No. 13/885,178 to inventors Sven Krause et al. provides a gas spectrometer having a cylindrical multipass cell with two opposing end-mirrors in a tubular chamber (i.e., cell cavity) that tapers from a gas inlet end toward a gas outlet end. U.S. patent application Ser. No. 10/081,655 to inventors James T. Daly et al. provides an absorption spectroscopy apparatus incorporating a multipass cell that has a curved reflective inner side wall surface; here, a beam of energy is reflected off the reflective surface axially in substantially the same plane inside the cell. U.S. Pat. No. 5,291,265 to Kebabian employs astigmatic mirrors, and provides for mirror manufacturing errors to be resolved by adjusting mirror separation and twist angle. U.S. Pat. No. 7,800,751 to inventors Silver, et al. provide a two end-mirror optical cell and method employing cylindrically curved mirrors; the cell has an inlet hole on the first end-mirror and an outlet hole at approximately the center of an opposing second end-mirror, forming a lissajous spot pattern on the end-mirrors. Finally, U.S. Pat. No. 8,531,659 to inventors Stephen So, et al. employs spherical aberration to advantage, and utilizes an "iterative artificial intelligence-based optimization" to create spot patterns for a particular, selected multipass cell configuration.

Unfortunately, the above and other optical multipass systems are found by the present inventors to be unduly limited by the particular multipass cell type, and have heretofore proven incapable of achieving a more compact size, different/variable geometry, lesser complexity and/or useful manipulation of subject samples, sources, detection, computational systems and/or other characteristics. Such deficits not only result in limited multipass system arrangement, size and/or other constraints, but also result in greater cost, for example, where control of temperature, pressure and/or other environmental aspects are exacerbated by greater size, or where portability, operational feasibility and/or other factors are negatively impacted. Requisite use of custom mirrors, grinding and/or other optics can also reduce flexibility, increase cost, and so on, among yet further disadvantages.

Accordingly, there is a need for optical multipass cell, spectrometer and/or other optical multipass systems and methods that enable a long optical path in a very small multipass cell size or variable geometry/configuration. There is also a need for optical multipass systems and methods that enable production of high density optical patterns while avoiding optical interference, that are capable of lower-cost production/operation, and/or that enable combinations of the above and/or other disadvantages of the above and/or other conventional\emerging systems to be avoided and/or further advantages to be achieved.

SUMMARY

Embodiments of the present invention provide optical multipass systems and methods that enable long effective optical paths and high optical pattern density in very small system geometries and/or variable configurations. Examples can be utilized in optical multipass cell configurations based on different underlying cell types and/or in manners that deviate from size, geometry and/or configuration/arrangement constraints of conventional multipass cells, thereby enabling disadvantages of conventional/emerging multipass systems to be avoided and/or further advantages to be achieved.

In various embodiments, an optical multipass system is configured to include, in addition to an end-mirror configuration of reflective surfaces (also referred to herein as "end reflective surfaces"), a further multipass pattern folding assembly. The end-mirror configuration provides for cell stability and directing/focusing, while the further multipass pattern folding assembly provides for folding an optical pattern intra-cavity at least twice off of a single mirror surface. The multipass pattern folding assembly in various embodiments includes at least two folding reflective surfaces (also referred to herein as "inner reflective surfaces" or "folding inner reflective surfaces") interposed as optically inner surfaces in an optical path extending between at least two other reflective surfaces, such that an optical pattern is directed two or more times toward at least one of the folding inner reflective surfaces and thereby folded there-between. Embodiments thus enable the physical extent of the multipass cell, multipass cell incorporating and\or other multipass system to be reduced while at least maintaining an optical path length otherwise sought, for example, by instead increasing the distance between the end-mirrors. Among other aspects, ones\ combinations of such embodiments are also operable in conjunction with a laser light source and/or a denser resulting optical pattern.

In some embodiments, the end reflective surfaces are configured to form a stable optical cavity in accordance with a Herriott cell type base configuration, and at least one of the end reflective surfaces comprises a spherical or astigmatic end mirror or other reflective surface. The folding inner reflective surfaces in some embodiments include at least two substantially flat mirrors or other reflective surfaces that are, in various embodiments, disposed substantially parallel to one another. It will become apparent to those skilled in the art, however, that other cell types are also similarly configurable and operable in conjunction with at least one folding assembly. It will also become apparent that various component variations and/or configurations are also similarly supportable, only a portion of which might be specifically noted herein. Among other examples, various optical multipass system embodiments include laser gas spectrometers and/or other applications that include an optical multipass cell in accordance with the teachings herein.

(Note that the term "or", as used herein, can mean "and/or" unless specifically noted or otherwise clearly denoted by the surrounding description, whether or not the term "and/or" merely happens to appear as well.)

Accordingly, an optical multipass system according an embodiment of the invention includes at least two end reflective surfaces in which at least one of the end reflective surfaces is or includes a focusing surface for forming a stable optical cavity, and in which each end reflective surface is configured to direct an optical multipass pattern (i.e., or various stages of generating such pattern) two or more times toward at least one of folding inner reflective surfaces. The optical multipass system also includes at least two folding inner reflective surfaces configured to fold an optical path of a resulting multipass pattern intra-cavity between the end reflective surfaces. In a more specific embodiment, each of the at least two end reflective surfaces is configured to direct the optical multipass pattern toward a respective one of the folding reflective surfaces; the folding reflective surfaces are further configured such that the optical path is folded repeatedly between the folding reflective surfaces during each of a pre-configured number of "passes". Among other embodiments, various examples provide such a configuration as consisting of two simple or compound end-mirrors disposed at longitudinally opposing ends of a folding assembly in which the folding assembly consists of two substantially parallel and substantially flat rectangular or otherwise elongated folding mirrors.

While the apparatus and method has or will be described for the sake of grammatical fluidity with functional explanations, it is to be understood that the claims, unless expressly formulated under 35 USC § 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC.sctn.112 are to be accorded full statutory equivalents under 35 USC § 112.

The invention and its novel features can be better understood by turning now to the following drawings, taken in conjunction with the accompanying description, in which similar elements are referenced by similar numerals. Reference throughout this specification to "one example," "an example," "one embodiment,", "an embodiment", "embodiments" or "various" or "some" embodiments means that a particular feature, structure, or characteristic described in connection with the example is included in at least one example of the present technology. Thus, occurrences of the such phrases in this specification are not necessarily all referring to the same example. Furthermore, the particular features, structures, routines, steps, or characteristics may be combined in any suitable manner in one or more examples, and headings provided herein are for convenience only and are not intended to limit or interpret the scope or meaning of the claimed technology.

BRIEF DESCRIPTION OF THE DRAWINGS

In the drawings, like reference characters may generally refer to the same or similar elements throughout the different views. The drawings are not necessarily to scale, with an emphasis instead generally being placed upon illustrating the principles of the invention. Likewise, arrows that might be depicted as pointing in a particular direction are also merely exemplary and should not be construed as limiting, but instead as merely illustrative for the purpose of conveying a better understanding of the principles of the invention.

In the following description, various embodiments of the present invention are described with reference to the following drawings, in which.

DETAILED DESCRIPTION

The terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating aspects disclosed herein may be used in whole or part without departing from the spirit and scope of the invention. Accordingly, the described embodiments are to be considered in all respects as merely illustrative and not restrictive.

In providing for optical multipass systems and methods that enable long effective optical paths, high optical pattern density, smaller system geometries and/or other advantages, aspects of the invention depart from those of conventional systems that are, for example, discovered to be unnecessarily reliant on limitations imposed by particular underlying multipass cell types and/or operable in conjunction with only a particular underlying multipass cell type.

Figure 1:
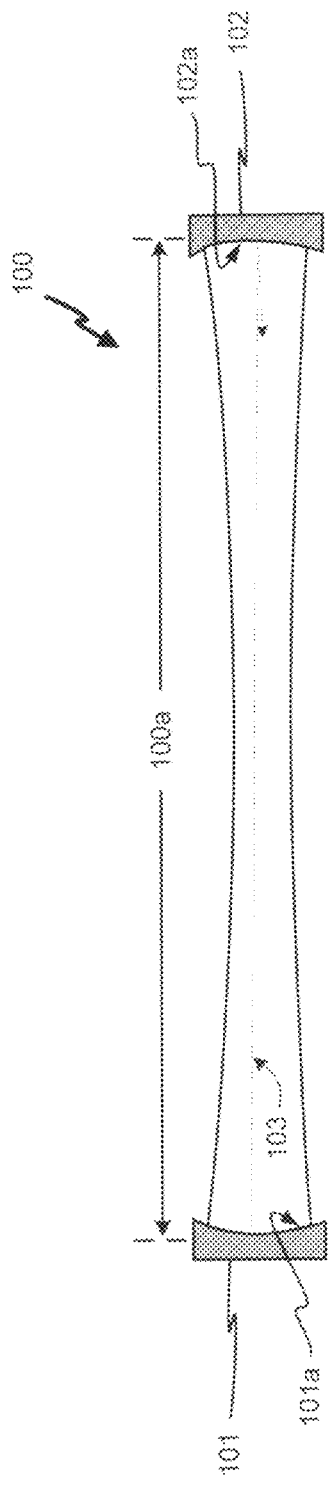
FIG. 1 is a simplified illustration of a prior art Herriott cell type (also referred to herein as a "Herriott cell") according to an embodiment of the present invention.

FIG. 1, for example, shows how the arrangement of components in a conventional Herriott cell 100 attempts to achieve a long optical path by employing a (correspondingly) sufficiently long cell cavity length 100a and causing a source light beam 103 to reflect directly between curved reflective surfaces 101a, 102a of first and second curved end-mirrors 101, 102 (e.g., as indicated by the dashed line) that are disposed at opposing ends of the long cell cavity. Here, the optical path, characteristic response, stability and achievable optical path length, of cell 100 are all effectively dictated by positioning suitable end-mirrors 101 and 102 at each end of a sufficiently long cell cavity. Therefore, the cavity length 100a for achieving a long optical path with low interference, and thus the dimensions of cell 100, are determined exclusively by the number of low interference reflections (also referred to herein in terms of "bounces") that are achievable through repeated reflection along an optical path that extends directly between the two end-mirrors 101, 102 positioned at the opposing ends (lengthwise) of the elongated cell cavity, according to the surface characteristics of end-mirrors 101, 102. (Note that the light ray pattern typically occurring between the end-mirrors when aligned with a specific geometry is schematically represented by a solid object.) It is well known that the per-pass rotation of the spots (θ) around the resultant elliptical spot pattern formed on each mirror (assuming equivalent mirrors) is given by $$\theta = \cos^{-1}(1 - d/R),$$

where d is the mirror spacing, and R is the radius of curvature. In general, the beam will exit the entrance hole after a prescribed number (n) of round-trip passes when the following condition is met:

$$2n\theta = 2m\pi,$$

where m is an integer.

It will be appreciated that Herriott cell 100 also typically includes additional components that are omitted here for clarity sake. For example, a Herriott cell typically utilizes suitable mechanisms for introducing a source light beam and for exiting of a resulting optical pattern from the cell, e.g., an inlet-outlet in one of end-mirrors 101, 102 or a separate inlet and outlet disposed within respective ones of end-mirrors 101 and 102. Herriott cell 100 might also utilize a suitable light source, enclosure, mounting assembly, lens(es), window(s), and so on, and in a gas absorption spectrometer or other applications, a sample flow mechanism, temperature control, local\remote control, measurement, data gathering, network, storage and\or other computing component and\or system hardware\software, and so on. It will also be appreciated that such elements would in practice be selected in accordance with cost, performance, application, sampling, cavity environment and/or other requirements of a particular implementation.

For consistency, the discussion herein will continue to focus on multipass systems based on a Herriott cell type and having a particular, suitable exemplary configuration, so that aspects of the invention might be better understood. Those skilled in the art will, however, appreciate that cavity length, portability, component integration, optimization and/or other limitations similar to those presented by the Herriott cell have also heretofore existed for other underlying multipass cell types as well as other multipass systems based on the Herriott cell and other multipass cell types, including but not limited to those specifically noted herein. It will also become apparent as the discussion progresses that aspects of the present invention are also useable in conjunction with these and/or other existing/emerging multipass cell and/or other multipass system configurations and/or other aspects in accordance with the requirements of a particular implementation, only a subset of which might be specifically discussed.

Figure 2:
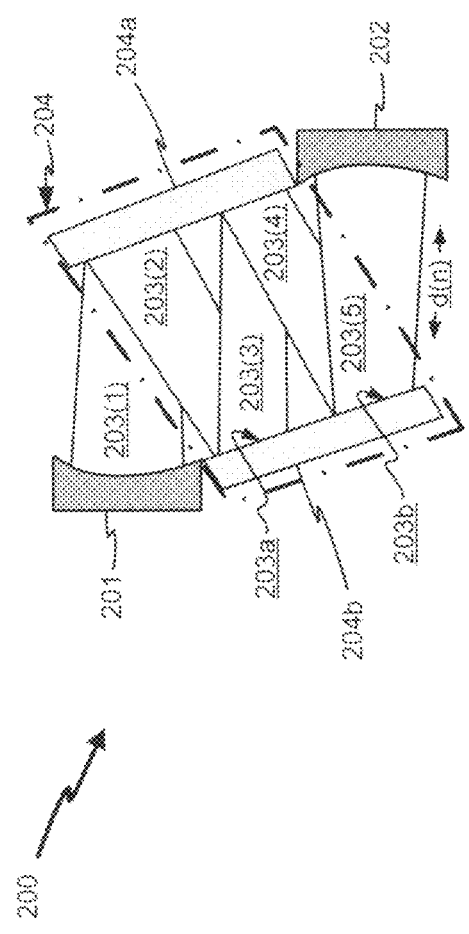
FIG. 2 is a simplified illustration of a folded optical multipass configuration according to an embodiment of the invention that is further producible using the folded optical multipass system embodiment of FIG. 3.

FIG. 2 shows how a substantially reduced requisite physical cavity size (or system size) can be achieved as compared to, for example, the Herriott cell of FIG. 1 or other underlying optical multipass system types, resultant multipass cells or other resultant multipass systems that provide substantially the same (or a lesser or greater) optical path length. Optical pattern folding according to an embodiment of the invention introduces additional optical surfaces along the optical path connecting, for example, a first end-mirror disposed at a first end of a long cavity (e.g., end-mirror 201) and a second end-mirror disposed at the opposing end of the cavity (e.g., end-mirror 202). While end-mirrors, other reflective surfaces and/or other optics can continue to be configured for establishing system stability, arrangement and/or other purposes, and without thwarting such configuration\purposes, the additional optical surface combination (here, only a single "pattern-folding assembly" 204 and including two reflective surfaces 204a, 204b as shown) instead provides for folding the optical pattern. In doing so, optical multipass system 200, here, an optical multipass cell, thereby provides for substantially reducing the requisite physical extent of the cell (or an apparatus incorporating the cell) while maintaining the overall optical path-length, e.g., as compared with length 100a of exemplary cell 100 of FIG. 1. It will also become apparent to those skilled in the art that a resulting optical pattern produced by the illustrated or other configurations can also be similarly folded (e.g., bouncing at least twice off at least one of folding assembly elements 204a, 204b according to the illustrated configuration). The FIG. 2 example further shows how such configurations can cause the light source to bounce at least twice off at least one of the folding assembly elements during each of a multiplicity of passes, and in an indirect path between end reflective surfaces, e.g., 201, 202 (as opposed, for example, to the direct path 103 between surfaces 101a and 102a of FIG. 1).

(As noted, embodiments of the invention are also applicable to such optical cell types that also can include differing numbers and\or types of end reflective surfaces (e.g. astigmatic surfaces) and/or other components. See, for example, the above-noted U.S. Pat. No. 5,440,143 to inventors Carangelo, et al., U.S. Pat. No. 5,291,265 to inventors Kebabian, et al., U.S. Pat. No. 7,800,751 to inventors Silver, et al., and U.S. Pat. No. 8,531,659 to inventors Stephen So, et al.).

Figure 3:
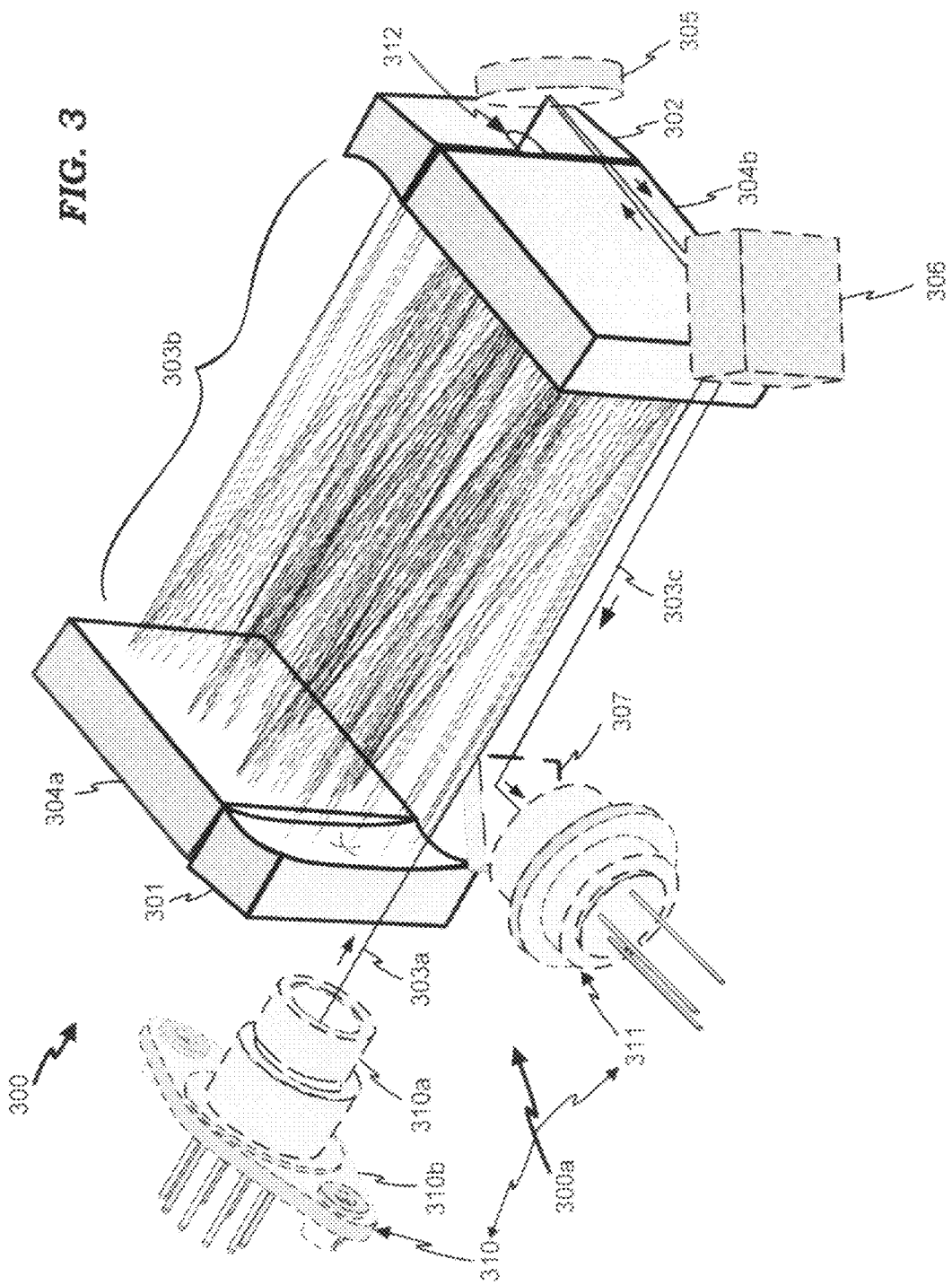
FIG. 3 is a perspective view of a folded optical multipass system, according to an embodiment of the present invention.
Figure 4:
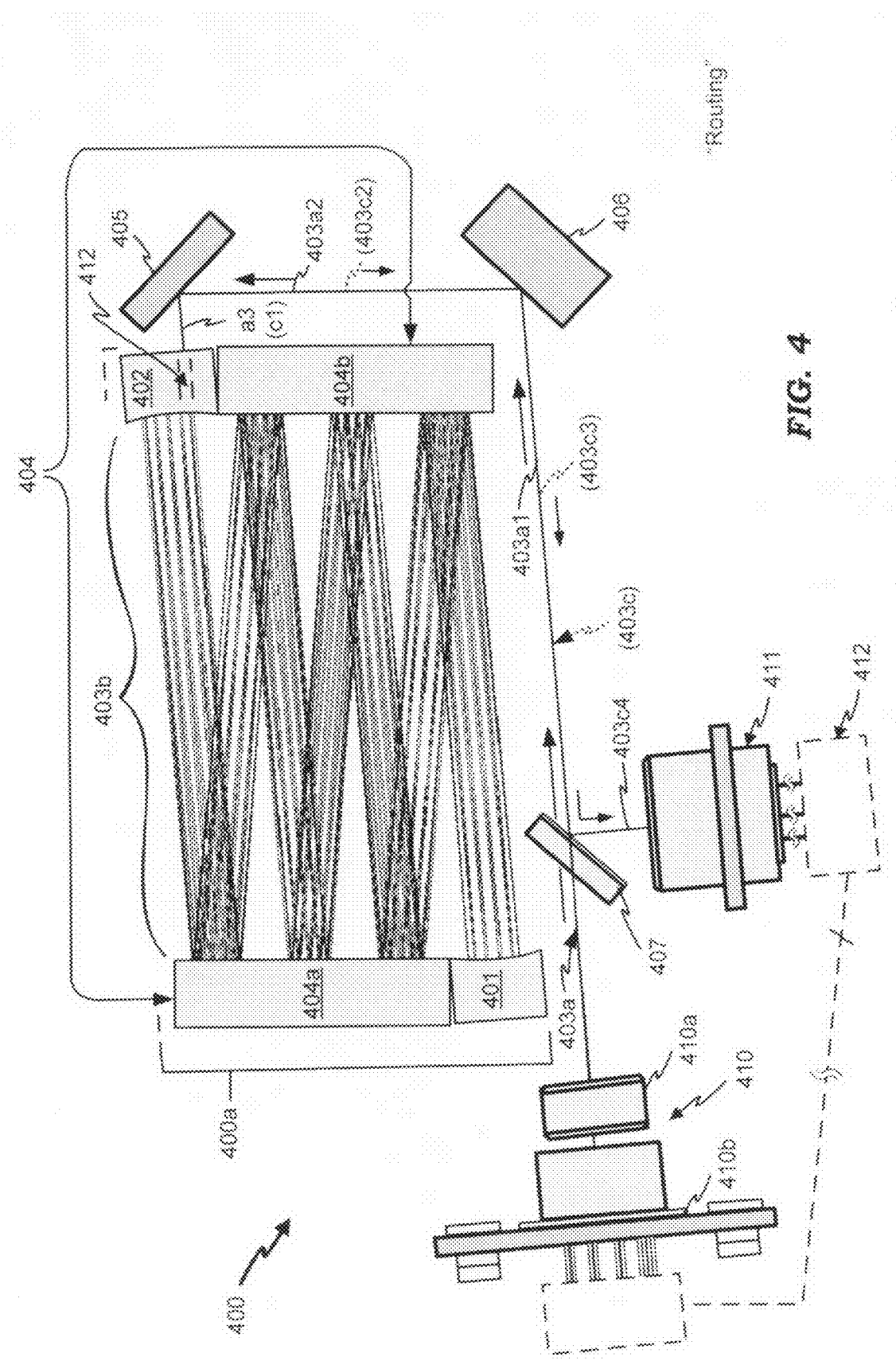
FIG. 4 is a top view of the folded optical multipass system in FIG. 3 according to an embodiment of the present invention.

Continuing now with FIGS. 3-4, there are illustrated further embodiments of optical multipass systems that are capable of utilizing an underlying Herriott cell (or other cell type) according to aspects of the invention. As was already noted, aspects of the invention enable a wide variety of optical multipass systems, for example, various optical multipass cells as well as various spectrometers and still further systems, for example, incorporating optical multipass cells, according to embodiments of the invention. Thus, in order to further illustrate an example of how such flexibility can be exploited, FIG. 3 employs solid lines to denote components used in an exemplary optical multipass cell 300 (here, having an underlying Herriott configuration) and then further employs dashed lines to denote an example of additional components that can be used in conjunction with an open-air or closed-system optical spectrometer or other system(s) 300a incorporating optical multipass cell 300. Similarly, FIG. 4 uses solid lines to illustrate an optical spectrometer 400 example employing the optical multipass cell of FIG. 3 (here, denoted as 400a) and other components of FIG. 3, along with additional components. Common components are similarly numbered in FIGS. 3-4. FIGS. 3 and 4 also provide complimentary views for better illustrating, in one figure, different or somewhat obscured aspects as illustrated by the other figure.

FIG. 3, for example, shows an optical multipass cell embodiment 300 using solid lines, along with further exemplary elements of multipass system 300a shown using dashed lines and which further elements are also shown in FIG. 4, but using solid lines in FIG. 4. Such elements include exemplary optical routing elements, for example, routing mirrors and/or other reflective surfaces 305-306 (405-406 of FIG. 4) suitable for routing an indirect light source to multipass cell 300 of FIG. 3 (or cell 400a of FIG. 4) at a suitable angle of incidence to a cell inlet, e.g., inlet-outlet 312 (or inlet-outlet 412 of FIG. 4), and/or for routing a resulting optical pattern from a cell outlet, window, etc., e.g., inlet-outlet 311 of cell 300 of FIG. 3 (or inlet-outlet 412 of cell 400a of FIG. 4) to a further extra-cell application element or elements. (It will be appreciated by those skilled in the art that one or more lenses\other components can also be utilized for capturing, directing and\or modifying intermediate and\or resulting optical pattern(s) in accordance with the requirements of a particular application) Also included are exemplary: light source 310, 410 (e.g., a laser emitter including lens 310a or 410a) and representative detection or further control/analysis elements 311, 411 (e.g., a photo detector) that are useable in conjunction with various multipass systems 300a incorporating multipass cell 300 in accordance with the requirements of various applications.

FIGS. 3-4 also show how an embodiment of the present invention is configurable for utilizing a Herriott cell to form a base Herriott cell pattern as an ellipse, rather than a circular arrangement of spots, as is commonly employed in conjunction with multipass cells. The simplified diagram in FIG. 5, for example, shows how suitable reflective surfaces, such as the exemplary concave end reflective surfaces of the FIG. 3 and FIG. 4 embodiments can produce an elliptical pattern that can be employed to significantly compress the spatial extent of the patterns along one axis and thereby achieve a significantly higher effective spot density on the reflective surfaces.

Returning now to FIG. 3, multipass cell 300 comprises end reflective surfaces and a folding assembly including inner reflective surfaces for folding the multipass pattern (also referred to herein as simply "folding inner reflective surfaces") that are configured within an optical path between the end reflective surfaces, thus giving rise to the term "inner". In accordance with the illustrated configuration, two end reflective surfaces 301, 302 are provided that, along with folding assembly 304 (including two folding inner reflective surfaces 304a, 304b) together define a folding region 303b in which optical pattern folding occurs in a manner corresponding to the component configuration, and particularly, the folding assembly configuration. For convenience and in accordance with end reflective surface 302 defining an inlet-outlet 312 through which cell 300 receives a light source (the light source further being emitted by emitter 310 and received indirectly via routing reflective surfaces 305-306), end reflective surfaces 302 and 301 will be referred to respectively as a or the "first" end reflective surface and a or the "second" end reflective surface.

In this example, a Herriott cell is selected as an underlying cell type and efforts are made to further minimize cost and complexity by attempting to maintain a low component count, repeated elements and compact configuration; similarly, the use of off-the-shelf elements is also desirable in accordance with such design constraints. Thus, while at least one of end reflective surfaces 301, 302 is preferably curved, e.g., concave or astigmatic, a suitable configuration is also achievable with the illustrated two concave end reflective surfaces. Similarly, two substantially flat folding inner reflective surfaces 304a, 304b are also provided that are substantially parallel to one another, in accordance with the present example. Finally, while other suitable configurations including but not limited to those discussed herein (e.g., using a separately disposed inlet and outlet, window, different placements, and so on), end reflective surface 302 defines an inlet-plus-outlet opening positioned generally as shown and that is capable of receiving a light source and also permitting egress of a resulting optical pattern, with the receiving and egress rays naturally occurring at separate and distinct angles with respect to each other.

It will be appreciated, however, that various alternative configurations can also be used that might be found useful in accordance with a different underlying cell type characteristics, enclosure, mounting assembly, use of other optics and/or other elements, sampling and/or other requirements of a particular multipass system implementation. For example, with regard to even the illustrated reflective surfaces, the reflective surfaces can comprise simple and/or compound (off-the-shelf, custom and/or customized composite or multiple) mirrors, metallic or other coatings and/or other reflective surfaces having suitable reflective properties for operating in a particular multipass cell implementation. More than two end reflective surfaces and/or more than two folding inner reflective surfaces and/or folding assemblies can also be used. It will also be appreciated that other embodiments might utilize other, more suitable, custom or customized end reflective surface geometries, surfaces and/or configuration for producing particular optical patterns and/or meeting other constraints of a particular implementation. Other embodiments can also position even the illustrated substantially flat and substantially parallel folding inner reflective surfaces at different distances apart or utilize non-parallel, angular or otherwise varying separation and/or other surface geometries, so long as the overall cavity geometry remains stable. Other alternatives will also become apparent to those skilled in the art in view of the discussion herein.

Enclosure and mounting details are not shown in the drawings for clarity sake, so that aspects of the invention might be better understood. However, those skilled in the art will appreciate that any suitable enclosure(s) and/or mounting assembly or assemblies can be utilized, including but not limited to those discussed herein, in accordance with the requirements of a particular application. For example, a suitable enclosure for a particular gas analysis application or applications might include a complete or partial enclosure, or even no enclosure. A suitable enclosure can also include fixed or fully/partially adjustable and/or mechanized mounting assemblies and can further include a suitable mechanism for receiving/expelling fluid samples, a window and/or access mechanism for facilitating alignment, detection and/or other purposes, and so on. Examples also include fully/partially integrating all or a subset of multipass system elements directly to a suitable enclosure and/or separate mounting assembly portions, selecting more or less rugged or otherwise specialized enclosure/assembly materials and/or intra and/or extra cavity environmental mechanism in conjunction with particular sample types, mechanisms for measuring temperature, pressure and/or other requisite parameters, and so on. Various existing or emerging mechanical and\or other mounting can also be used for adhering or otherwise coupling system 300, 300a components, as will also typically be determined according to particular application constraints. Those skilled in the art will further appreciate that some combination of these and/or other elements might also be utilized according to particular implementation goals, parameters and/or other considerations.

Returning now to FIG. 3, folding assembly 304 is configured to comprise at least two substantially flat folding inner reflective surfaces, positioned substantially in parallel to one another, as shown respecting folding inner reflective surfaces 304a and 304b. First and second folding inner reflective surfaces 304a and 304b are further configured such that a multipass pattern is received by a first folding inner reflective surface (e.g., 304a).

The folding inner reflective surfaces configuration causes the light pattern received by the first folding inner reflective surface to be folded a multiplicity of times by reflecting the light beams between the folding inner reflective surfaces in an optical path that traverses the folding assembly, and then directs the light beam to one of the end reflective surfaces. In particular, the configuration causes the optical pattern to bounce at least twice from at least one of the folding inner reflective surfaces during a single traversal of the folding assembly.

The second end reflective surface (e.g., 301) is configured to receive, from the folding assembly, the light beam as redirected by the first end reflective surface (e.g., 302) and having traversed the folding assembly, and to redirect the light beam back toward the folding assembly such that the light beam is again similarly folded by folding inner reflective surfaces during a traversal of the light beam through the folding assembly, and then directed toward the first end reflective surface (e.g., 302). The first end reflective surface (e.g., 301) is further configured to receive the light beam from the folding assembly and, in all instances except a final instance, to redirect the light beam back toward the folding assembly, such that: the light beam is again similarly folded by the folding assembly during each successive traversal of the light beam through the folding assembly, and is then directed toward the second end reflective surface (e.g., 302). In a more specific example, such configuring causes the first end reflective surface to redirect the light beam so as to conform to an optical path pattern that avoids overlapping other reflection points within the folding assembly, and to advance a resulting optical pattern that is selected to be produced according to the configuring of the optical multipass cell elements. (As was already noted, in various embodiments the first and/or second end reflective surfaces are also configured as spherical or astigmatic and both are further configured according to dimensioning, surface(s), orientation, positioning, and so on, for providing cell stability and otherwise in accordance with the requirements of a particular application. See, for example, FIGS. 3-5) The configuring of the reflective surface elements further causes a resulting optical pattern to exit the multipass cell via the provided outlet or inlet-outlet (e.g., inlet-outlet 312 defined by end reflective surface 302).

Figure 5:
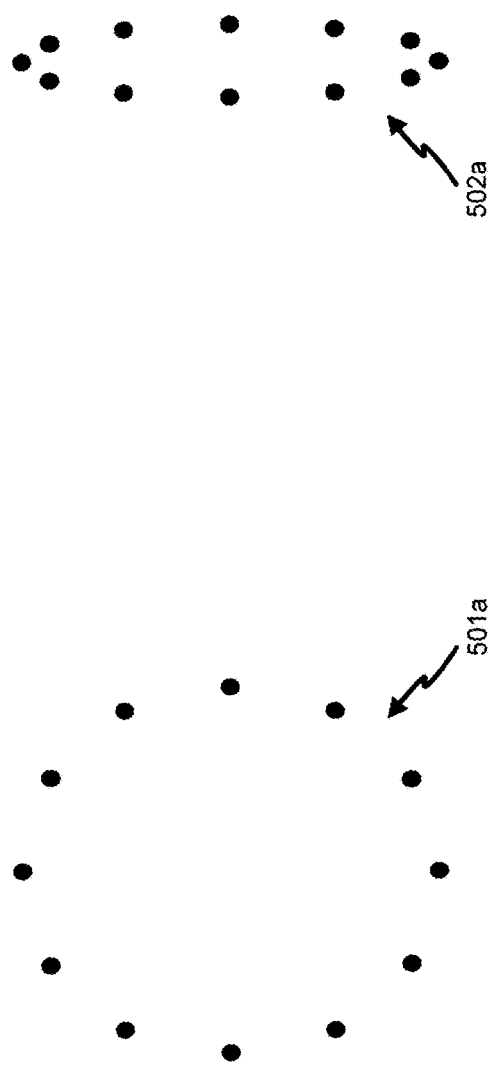
FIG. 5 graphically illustrates examples of circular and elliptical optical spot patterns commonly obtained in Herriott cells, and how folded optical multipass system embodiments enable the optical patterns to be projected successive times onto at least one folding inner reflective surface and the optical path length thereof thereby increased, without requiring an increased cavity length, according to an embodiment of the invention.
Figure 5:
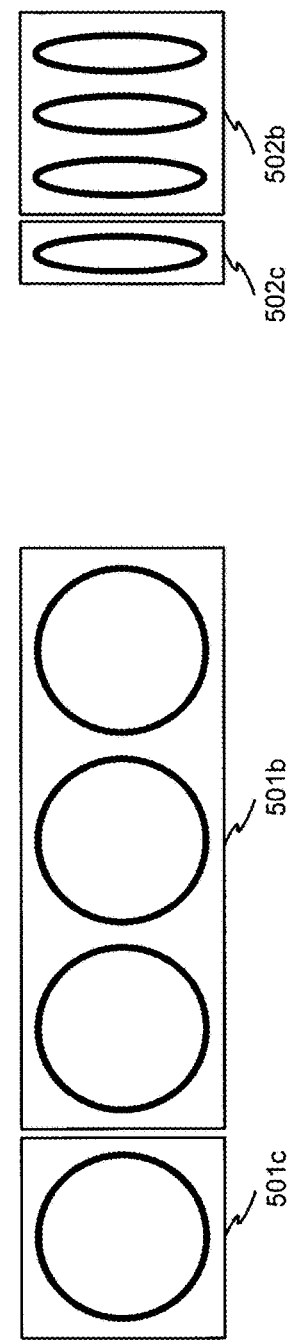

FIG. 5 illustrates a further, more specific example in which such configuration causes the optical pattern to be reflected from each folding inner reflective surface three times. Under optimal conditions, this serves to reduce the physical length of the cell by a factor of 7, at the expense of a 4× increase in width. However, as typical Herriott cells tend to be long and thin, this exchange of width for length can be quite advantageous in terms of overall system size. While the more specific example provides an advantageous, high density and more compact elliptical spot pattern, those skilled in the art will appreciate that such configuring (e.g., end reflective surface geometry, position, direction and so on) can also be selected to produce circular and/or other differing pattern/density optical patterns in conjunction with multipass pattern folding, folding assembly, folding multipass cell and/or other aspects of the present invention.

For example, the optical pattern folding technique disclosed here could alternately be employed with a White cell type base configuration. Specifically, a two-mirror intracavity folding assembly could be employed to reduce the physical length of a White cell by similarly reflecting the intracavity pattern at least twice off of at least one of the intracavity folding mirrors (e.g., in a same or similar manner as with the folding assemblies of FIGS. 3 and 4). Additionally, as a typical three-mirror White cell produces an optical pattern with a somewhat rectangular cross-section, projecting or "stacking" the pattern on the folding mirrors along the shorter side of the rectangle (similarly to that shown in FIG. 5 for the exemplary elliptical spot pattern) could therefore, in principal, produce a significantly denser optical pattern to be achieved, allowing for more compact overall assembly.

Turing now to FIG. 4 with further reference to FIG. 3, in a more specific embodiment, the reflective surfaces are configured such that an optical path produces a zig-zag path of rays between the folding inner reflective surfaces, an example of which can be more clearly seen with reference to FIG. 4. Here, an exemplary multipass system 400 for implementing a particular application is illustrated, i.e. laser gas spectroscopy, according to an embodiment of the invention. As shown, laser gas spectrometer 400 comprises a multipass cell 400a, an optical routing assembly including exemplary routing optics 405-407 light source 410, photo detector 411 and representative control/analysis module 412. For consistency, multipass cell 400a is configured in a similar manner as with multipass cell 300 of FIG. 3, including a similarly configured folding assembly 404 for folding a light source in the manner already discussed with reference to FIG. 3, similarly configured end reflective surfaces 401, 402 and a similarly configured optical inlet-outlet 412 defined by end reflective surface 402.

As with various other multipass system applications utilizing a multipass cell according to the invention, typically a light source should also be provided along with optical routing in order to provide indirect application of the light source to the multipass cell. Light emitter 410 also includes lens 410a and mounting hardware 410b. Light emitter 410 can further be electrically coupled or couple-able to controller-analyzer 412. (It will be appreciated that other light source(s) and/or light source component(s) can also be used in accordance with the requirements of a particular implementation.)

The illustrated optical routing assembly example comprises optics including reflective surfaces 405, 406 and 407. As can also be seen with reference to FIG. 4, a laser light source provided by emitter 410 is routed along an exemplary light path 403a about a portion of a perimeter of multipass cell 400a and in close proximity to multipass cell 400a, in accordance with the exemplary optical routing assembly configuration.

As a result, light path 403a of the light source passes over reflective surface 407 to reflective surface 406 (path segment 403a1) which reflects the light source to reflective surface 405 (path segment 403a2). The configuring of reflective surface 405 further causes the received light source to be reflected suitably off axis via inlet 312 of FIG. 3 (path segment (403a3) and received intra-cavity by multipass cell 400a in the manner already discussed. Similarly, an optical pattern produced by multipass cell 400a is again routed in close proximity to the multipass cell perimeter, in a light path substantially similar to the light source routing, and can utilize the same optical assembly components 405, 406. Specifically, the resulting optical pattern exiting multipass cell suitably off-axis through inlet-outlet outlet 412 or 312 of FIG. 3 (path segment 403c1) is routed by reflective surface 405 along path 403c2 to reflective surface 406. Reflective surface 406 further routes the resulting optical pattern along path segment 403c3 to reflective surface 407, which routes the resulting optical pattern along path segment 403c4 to light detector 411. While other routing alternatives might also be used alone or in conjunction with the present example, it will be appreciated that the exemplary configuration provides for a very compact form factor in which a light source and/or resulting optical pattern are provided to corresponding multipass system components indirectly.

Photo-detector 411 provides for receiving the light produced by laser light source 410 after the light has traversed the entire optical path (i.e., including the aforementioned routing from emitter 410 to cell 400a, within cell 400a and routing from cell 400a to photo-detector 411). Photo-detector 411 can further be electrically coupled or couple-able to controller-analyzer 412. (It will be appreciated that any suitable photo-detector or detectors can be used in accordance with the requirements of a particular implementation.)

At least one suitable control/analysis module 412 can be provided for initiating, affecting the operation of, synchronizing, monitoring and/or otherwise operating applicable ones of emitter 410, detector 411 and/or other components of optical multipass system 400, in accordance with the requirements of a particular implementation. Without intending to be bound to specific use, component and/or other examples explicitly set forth herein, control/analysis module 412 can, for example, provide for operating implemented ones of determining, setting &/or varying emitter state and/or frequency, sample flow, component configuration\ adjustment, receiving output from light detector 411 and/or a window (not shown), determining testing criteria generally and\or for a specific location\sample, initiating\ conducting sampling, testing, determining, presenting and\or storing testing results and/or information corresponding thereto, and/or other operational purposes in accordance with the requirements of a particular application.

It will be appreciated that various components of control/analysis module 412 can also be configured in accordance with the requirements of a particular implementation. Factors such as size, cost, portability, modularization, distribution, general/specific standardization, durability, general\specific use, re-usability and/or other implementation goals (including but not limited to more specific open/closed cell, spectrometer, sampling, testing, pattern, light source, mounting and/or other examples noted elsewhere herein) can also apply to control/analysis module 412, and visa versa. Likewise, various control/analysis module 412 components can also be implemented as mechanical, electro-mechanical, electronic and/or can utilize one or more local/remote hardware\software (hereinafter referred to as computing systems) for control, synchronization, site, sample, test, system, user, result and/or other data-gathering, storage and/or other purposes. Where utilizing operating, firmware, application and/or other software, locally\remotely stored instructions and/or data can, for example, be directly and/or indirectly loaded in a suitable wired and/or wireless manner. Such information can, for example, be temporarily and/or more permanently stored on and loaded from a suitable computer-readable storage medium for execution by one or more suitable cpu's and/or other computing components of same or different computing systems. Any suitable computing system(s) using any suitable operating system (OS) can be used, including in conjunction with light detector 411 as well as any other suitable sensors, and suitable components can be statically and/or at least intermittently communicatingly coupled, for example, a via temporary or more permanent physical or virtual network or networks; suitable computing systems can, for example, include but are not limited to so-called smart phone, tablet, laptop, module and/or other more mobile or stationary and/or integrated, embedded and/or distributed computing system(s), i.e., and/or portions thereof.

It will further be appreciated that control/analysis module 412 and/or other spectrometer 400 components can be statically or removably affixed to same and/or different mounting assembly components (e.g., multipass cell 400a coupling to and/or being coupled to by one or more of these and/or other application related multipass system components) in a same or a similar manner as was already described for multipass cell 300 (FIG. 3). Further, same and/or different enclosures can also be used for multipass cell 400a and/or application related multipass system components in whole or part.

It will be apparent to those skilled in the art that various modifications and variations can be made in the system and method of the present invention without departing from the spirit or scope of the invention. Thus, it is intended that the present invention cover the modification and variations of this invention, provided they come within the scope of the appended claims and their equivalents.

What is claimed is:

1. An optical multipass system, comprising:
   at least two end reflective surfaces for forming a stable optical cavity; and
   at least two folding inner reflective surfaces disposed in an optical path between at least two of the end reflective surfaces for folding an optical multipass pattern, thereby enabling at least one of maintaining an optical path length while reducing a geometric extent of the optical multipass system, and increasing the optical path length while maintaining the geometric extent of the optical multipass system, wherein:
      herein at least one of the end reflective surfaces includes a focusing surface to form the stable optical cavity;
      at least one of the end reflective surfaces is oriented to direct an optical multipass pattern toward at least one of folding inner reflective surfaces in two or more passes between at least two of the end reflective surfaces; and
      at least two of the folding inner reflective surfaces are oriented within the optical path such that: at least one of the inner reflective surfaces receives the optical multipass pattern, and the optical multipass pattern is reflected by the at least two inner reflective surfaces and thereby folded intra-cavity between the end reflective surfaces at least twice during a single one of the passes between the at least two end reflective surfaces.

2. The optical multipass system of claim 1, wherein the optical system comprises an optical multipass cell.

3. The optical multipass system of claim 1, wherein the optical system comprises an optical gas spectrometer.

4. The system of claim 1, wherein the optical system comprises a Herriott cell base configuration.

5. The system of claim 1, wherein the optical system comprises a White cell base configuration.

6. The system of claim 5, wherein at least one of the end reflective surfaces is spherical.

7. The system of claim 5, wherein at least one of the end reflective surfaces is astigmatic.

8. The system of claim 1, wherein at least one of the end reflective surfaces is curved.

9. The system of claim 1, wherein at least one of the folding inner reflective surfaces is substantially flat.

10. The system of claim 9, wherein the compound reflective surface comprises at least one of the curved reflective surfaces.

11. The system of claim 10, wherein a folding region is optically defined by the end reflective surfaces and the folding inner reflective surfaces; further comprising one or more relaying reflective surfaces; and wherein the relaying reflective surfaces are configured to relay laser light from the laser light source to the folding region, and to relay the multipass cell pattern from the folding region to the optical detector.

12. The system of claim 11, wherein the multipass cell pattern that is relayed is an oval pattern.

13. The system of claim 1, wherein the folding inner reflective surfaces comprise two substantially flat reflective surfaces configured substantially in parallel to one another.

14. The system of claim 1, wherein at least one of the reflective surfaces is configured as a portion of a compound reflective surface.

15. The system of claim 1, further comprising a laser light source and an optical detector.

16. The system of claim 1, wherein at least one of the end reflective surfaces defines one or more openings along the optical path and allowing light to pass therethrough.

17. An optical multipass cell based on a Herriott cell type configuration, comprising:
    at least two curved end mirrors for forming a stable optical cavity; and
    at least two folding inner mirrors disposed in an optical path between the end mirrors for folding the optical path of an optical multipass pattern, thereby enabling at least one of maintaining an optical path length while reducing a geometric extent of the optical multipass system, and increasing the optical path length while maintaining the geometric extent of the optical multipass system, wherein:
       at least one of the end mirrors is oriented to direct the optical multipass pattern two or more times toward at least one of folding inner reflective surfaces in two or more passes between the end mirrors; and
       the folding inner mirrors comprise at least two substantially flat and substantially parallel folding inner mirrors oriented within the optical path such that: at least one of the inner reflective surfaces receives the optical multipass pattern; and the optical multipass pattern is reflected by the at least two folding inner mirrors thereby folding the optical path intra-cavity between the end mirrors at least twice during a single one of the passes between the end mirrors.

18. The optical multipass cell of claim 17, wherein:
    at least one of the end mirrors comprises a spherical focusing surface oriented for forming the stable optical cavity; and
    the at least two folding inner mirrors comprise two folding inner mirrors oriented so as to fold the optical path in a zig-zag path during a single pass between the end mirrors, thereby forming a resulting multipass pattern having a folded effective optical length.

19. An optical multipass cell based on a White cell type configuration, comprising:
    at least two curved end mirrors for forming a stable optical cavity; and at least two folding inner mirrors disposed in an optical path between the end mirrors for folding the optical path of an optical multipass pattern, thereby enabling at least one of maintaining an optical path length while reducing a geometric extent of the optical multipass system, and increasing the optical path length while maintaining the geometric extent of the optical multipass system, wherein:
- at least one of the end mirrors is oriented to direct the optical multipass pattern two or more times toward at least one of folding inner mirrors in two or more passes between the end mirrors; and
- the folding inner mirrors comprise at least two substantially flat and substantially parallel folding inner mirrors oriented within the optical path such that: at least one of the folding inner mirrors receives the optical multipass pattern; and the optical multipass pattern is reflected by the at least two inner reflective surfaces and the optical path is thereby folded intra-cavity between the end reflective surfaces at least twice during a single one of the passes between the at least two end reflective surfaces.

20. The optical multipass cell of claim 19, wherein:
at least one of the end mirrors comprises a spherical focusing surface oriented for forming the stable optical cavity; and
the at least two folding inner mirrors comprise two folding inner mirrors oriented so as to fold the optical path in a zig-zag path during a single pass between the end mirrors, thereby forming a resulting multipass pattern having a folded effective optical length.

* * * * *